US00PP16784P2

(12) United States Plant Patent
Bergman

(10) Patent No.: US PP16,784 P2
(45) Date of Patent: Jul. 11, 2006

(54) ***AZALEA* PLANT NAME 'SONNET'**

(50) Latin Name: *Rhododendron hybrida*
Varietal Denomination: Sonnet

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 38 days.

(21) Appl. No.: 11/119,042

(22) Filed: Apr. 30, 2005

(51) Int. Cl.
*A01H 5/00* (2006.01)

(52) U.S. Cl. ..... Plt./238

(58) Field of Classification Search ..... Plt./238
See application file for complete search history.

*Primary Examiner*—Kent Bell
(74) *Attorney, Agent, or Firm*—C. A. Whealy

(57) ABSTRACT

A new and distinct cultivar of *Azalea* plant named 'Sonnet', characterized by its dark green-colored leaves that do not abscise during the cooling and forcing periods; uniform and outwardly spreading plant habit; freely branching habit; uniform and freely flowering habit; relatively rapid flowering response; plants begin flowering about 33 days after cooling treatment; lavender-colored flowers with ruffled margins; double flower form; good postproduction longevity with plants maintaining good flower substance for about three weeks in an interior environment; and good resistance to *Cylindrocladium* in inoculated trials.

2 Drawing Sheets

Botanical designation: *Rhododendron hybrida.*
Cultivar denomination: 'Sonnet'.

BACKGROUND OF THE INVENTION

The present Invention relates to a new and distinct cultivar of *Azalea*, botanically known as *Rhododendron hybrida,* an evergreen greenhouse-forcing type *Azalea*, and hereinafter referred to by the name 'Sonnet'.

The new *Azalea* is a product of a planned breeding program conducted by the Inventor in Salinas, Calif. and Alva, Fla. The objective of the breeding program is to create new *Azalea* varieties having uniform plant habit, profuse and uniform flowering response, dark green foliage, good foliage retention during the cooling and forcing periods, resistance to *Cylindrocladium* and excellent postproduction longevity.

The new *Azalea* originated from a cross-pollination made by the Inventor in December, 1991, in Salinas, Calif., of a proprietary *Azalea* selection identified as code number YB-0607, not patented, as the female, or seed, parent with the *Azalea* cultivar Solitaire, disclosed in U.S. Plant Pat. No. 3,171, as the male, or pollen, parent. The new *Azalea* was discovered and selected by the Inventor as a flowering plant within the progeny of the stated cross-pollination in a controlled environment in Alva, Fla., in December, 1994.

Asexual reproduction of the new *Azalea* by terminal cuttings taken in a controlled environment in Alva, Fla. since April, 1995, has shown that the unique features of this new *Azalea* are stable and reproduced true to type in successive generations.

SUMMARY OF THE INVENTION

The new *Azalea* has not been observed under all possible environmental conditions. The phenotype may vary somewhat with variations in environment such as temperature, daylength and/or light intensity without, however, any variance in genotype.

The following traits have been repeatedly observed and are determined to be the unique characteristics of 'Sonnet'. These characteristics in combination distinguish 'Sonnet' as a new and distinct cultivar:

1. Dark green-colored leaves that do not abscise during the cooling and forcing periods.
2. Uniform and outwardly spreading plant habit.
3. Freely branching habit.
4. Uniform and freely flowering habit.
5. Relatively rapid flowering response; plants begin flowering about 33 days after cooling treatment.
6. Lavender-colored flowers with ruffled margins.
7. Double flower form.
8. Good postproduction longevity with plants maintaining good flower substance for about three weeks in an interior environment.
9. Good resistance to *Cylindrocladium* in inoculated trials.

In side-by-side comparisons conducted in Alva, Fla., plants of the new *Azalea* differed from plants of the female parent selection in the following characteristics:

1. Plants of the new *Azalea* were more vigorous than plants of the female parent selection.
2. Plants of the new *Azalea* flowered earlier after the cooling treatment than plants of the female parent selection.

In side-by-side comparisons conducted in Alva, Fla., plants of the new *Azalea* differed from plants of the male parent, the cultivar Solitaire, in the following characteristics:

1. Plants of the new *Azalea* were more upright and not as outwardly spreading as plants of the cultivar Solitaire.
2. Plants of the new *Azalea* and the cultivar Solitaire differed in flower color as plants of the cultivar Solitaire had pink-colored flowers.

Plants of the new *Azalea* can be compared to the plants of the cultivar Lavender Lace, disclosed in U.S. Plant Pat. No.

11,137. However, in side-by-side comparisons conducted in Alva, Fla., plants of the new *Azalea* differed from plants of the cultivar Lavender Lace in the following characteristics:

1. Plants of the new *Azalea* had darker green-colored leaves than plants of the cultivar Lavender Lace.
2. Plants of the new *Azalea* had double flowers whereas plants of the cultivar Lavender Lace had single flowers.

BRIEF DESCRIPTION OF THE PHOTOGRAPHS

The accompanying colored photographs illustrate the overall appearance of the new *Azalea*. These photographs show the colors as true as it is reasonably possible to obtain in colored reproductions of this type. Colors in the photographs may differ slightly from the color values cited in the detailed botanical description, which accurately describe the colors of the new *Azalea*.

The photograph on the first sheet comprises a side perspective view of a typical flowering plant of 'Sonnet'.

The photograph on the second sheet is a close-up view of typical flowers and leaves of 'Sonnet'.

DETAILED BOTANICAL DESCRIPTION

The aforementioned photographs and following observations and measurements describe plants grown in Alva, Fla. with three plants per 15-cm containers, in a polypropylene-covered shade house during the winter and early spring and under commercial production conditions. During the production of the plants, day temperatures ranged from 13 to 37° C. and night temperatures ranged from 0 to 26° C. Plants were pinched at planting, pinched a second time about twelve weeks later, and then pinched a third time about twelve weeks after the second pinch. After sufficient flower bud development, plants were cooled at 3 to 5° C. for about four weeks to break flower bud dormancy. Plants were subsequently forced into flower under commercial production conditions in a polyethylene-covered greenhouse. Plants used for the photographs and description were about one year old.

In the following description, color references are made to The Royal Horticultural Society Colour Chart, 2001 Edition, except where general terms of ordinary dictionary significance are used.

Botanical classification: *Rhododendron hybrida* 'Sonnet'.

Commercial classification: Evergreen greenhouse-forcing type *Azalea*.

Parentage:

*Female or seed parent.*—Proprietary *Rhododendron hybrida* selection identified as code number YB-0607, not patented.

*Male or pollen parent.*—*Rhododendron hybrida* cultivar Solitaire, disclosed in U.S. Plant Pat. No. 3,171.

Propagation:

*Type.*—By terminal vegetative cuttings.

*Time to initiate roots.*—Summer: About five weeks at temperatures of 24° C. Winter: About six weeks at temperatures of 24° C.

*Time to develop roots.*—Summer: About nine weeks at temperatures of 24° C. Winter: About eleven weeks at temperatures of 24° C.

*Root description.*—Fine, fibrous, and white in color.

*Rooting habit.*—Freely branching.

Plant description:

*Plant form and growth habit.*—Perennial, evergreen; uniform and outwardly spreading plant habit; broad inverted triangle; moderately vigorous growth habit. Densely foliated. Uniform and freely flowering habit with numerous double flowers per plant.

*Branching habit.*—Freely branching; about four primary lateral branches develop after the initial pinch (removal of terminal apex); numerous secondary and tertiary branches develop after the sequential second and third pinches.

*Plant height, soil level to top of flowers.*—About 27.5 cm.

*Plant diameter, area of spread.*—About 37 cm.

*Lateral branch description.*—Length: About 21 cm. Diameter at base: About 4 mm. Internode length: About 1.5 cm. Strength: Very strong. Texture, young: Pubescent, fine brown hairs. Texture, mature: Woody; pubescent, fine brown hairs. Color, young: Close to 144A. Color, mature: Close to 165A.

*Foliage description.*—Arrangement: Alternate, single. Foliage retention: Very good foliage retention on plants of the new *Azalea* that have been in a box for six weeks during the cooling treatment. Length: About 4.2 cm. Width: About 2.7 cm. Shape: Mostly elliptic. Apex: Cuspidate to mucronate. Base: Attenuate. Margin: Entire. Venation pattern: Pinnate. Texture, upper and lower surfaces: leathery, tough, durable; pubescent. Color: Developing and fully expanded foliage, upper surface: Darker green than 147A. Developing and fully expanded foliage, lower surface: Close to 147B. Venation, upper surface: Close to 147A; towards the base, close to 146A. Venation, lower surface: Close to 146A to 146B. Petiole: Length: About 7.5 mm. Diameter: About 3 mm. Texture, upper and lower surfaces: Pubescent. Color, upper and lower surfaces: Close to 146A to 146B.

Flower description:

*Natural flowering season.*—Spring after sufficient cool period. If forced, plants typically flower about 33 days after a four-week cooling treatment; relatively rapid flowering response. Flowers persistent.

*Flower arrangement.*—Flowers arranged singly at terminals with usually about four flowers per apex; uniform and freely flowering habit. Flowers face upward to mostly outward. Flowers rotate and rose-like.

*Flower appearance.*—Double flower form with a single outer whorl of petals and two to four inner whorls of petaloids (transformed stamens); petals and petaloids lavender in color.

*Fragrance.*—None detected.

*Flower diameter.*—About 5.6 cm.

*Flower depth.*—About 2.2 cm.

*Postproduction longevity.*—Good postproduction longevity; under interior conditions, plants maintain good flower substance for about three weeks.

*Flower bud (before showing color).*—Length: About 1.2 cm. Diameter: About 6 mm. Shape: Ovoid. Color: Close to 146A to 146B.

*Petals/petaloids.*—Arrangement: Double flower form; one outer whorl with about five imbricate petals and two to four inner whorls each with about five imbricate petaloids (transformed stamens); petals and petaloids fused at the base. Numerous whorls of petals and petaloids give a full, rose-like appearance to the flower. Petaloids variable in size and shape. Length, petals: About 3.3 cm. Width, petals: About 2.6 cm. Length, petaloids, center whorl: About 2.8 cm. Width, petaloids, center whorl: About 1.9 cm. Length, petaloids, inner whorl: About 2.1 cm. Width, petaloids, inner whorl: About 1.6 cm. Shape, petals and petaloids: Beyond fused base, roughly spatulate with rounded apex. Margin, petals and petaloids: Entire; undulate; ruffled. Texture, petals and petaloids, upper and lower surfaces: Smooth, glabrous; velvety. Color, petals and petaloids: When opening, upper and lower surfaces: Closest to N74A. Fully opened, upper lower surfaces: Closest to N74B to N74D.

*Sepals*.—Arrangement: Five in a single whorl, fused; subtending the petals. Length: About 6 mm. Width: About 5 mm. Shape: Spatulate. Apex: Acute. Texture, upper and lower surface: Pubescent. Color, upper surface: Close to 144A. Color, lower surface: Close to 146A.

*Peduncles*.—Length: About 2.3 cm. Diameter: About 2 mm. Angle: Mostly upright. Strength: Flexible; strong. Texture: Very pubescent. Color: Close to 144A.

*Reproductive organs*.—Androecium: None observed, typically all stamens transferred into petaloids. Gynoecium: Quantity of pistils per flower: One. Pistil length: About 1.1 cm. Style length: About 6 mm. Style color: Close to 144A. Stigma shape: Rounded. Stigma diameter: Less than 1 mm. Stigma color: Close to 144A. Ovary color: Close to 146A; heavily whiskered.

*Seed/fruit*.—Seed and fruit development have not been observed.

Weather/temperature tolerance: Plants of the new *Azalea* have been observed to be very tolerant to rain and wind. Plants of the new *Azalea* have been observed to tolerate temperatures from 0 to 38° C.

Disease/pest resistance: In inoculated trials that were conducted in Alva, Fla. during the summers of 1997, 1999, 2000 and 2004, plants of the new *Azalea* were observed to have good resistance to infection by *Cylindrocladium*. Plants have not been observed to be resistant to pests and other pathogens common to *Azaleas*.

It is claimed:

1. A new and distinct *Azalea* plant named 'Sonnet', as illustrated and described.

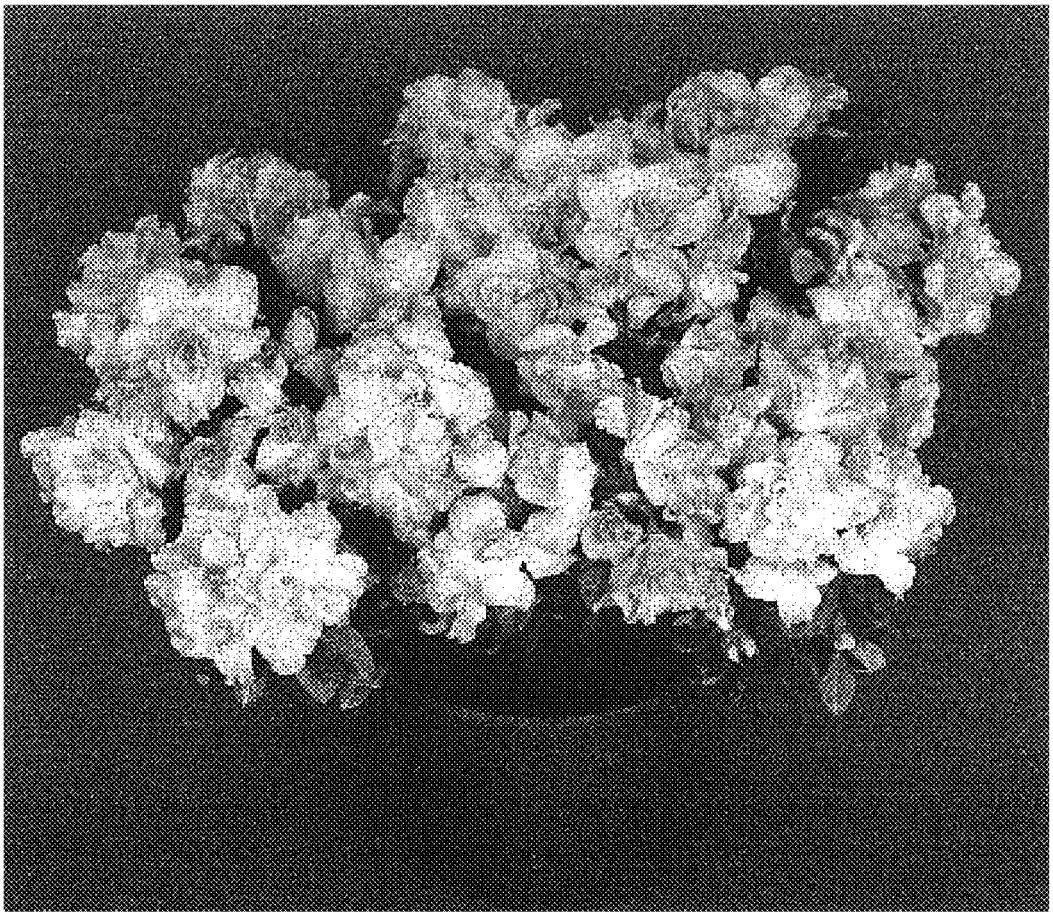

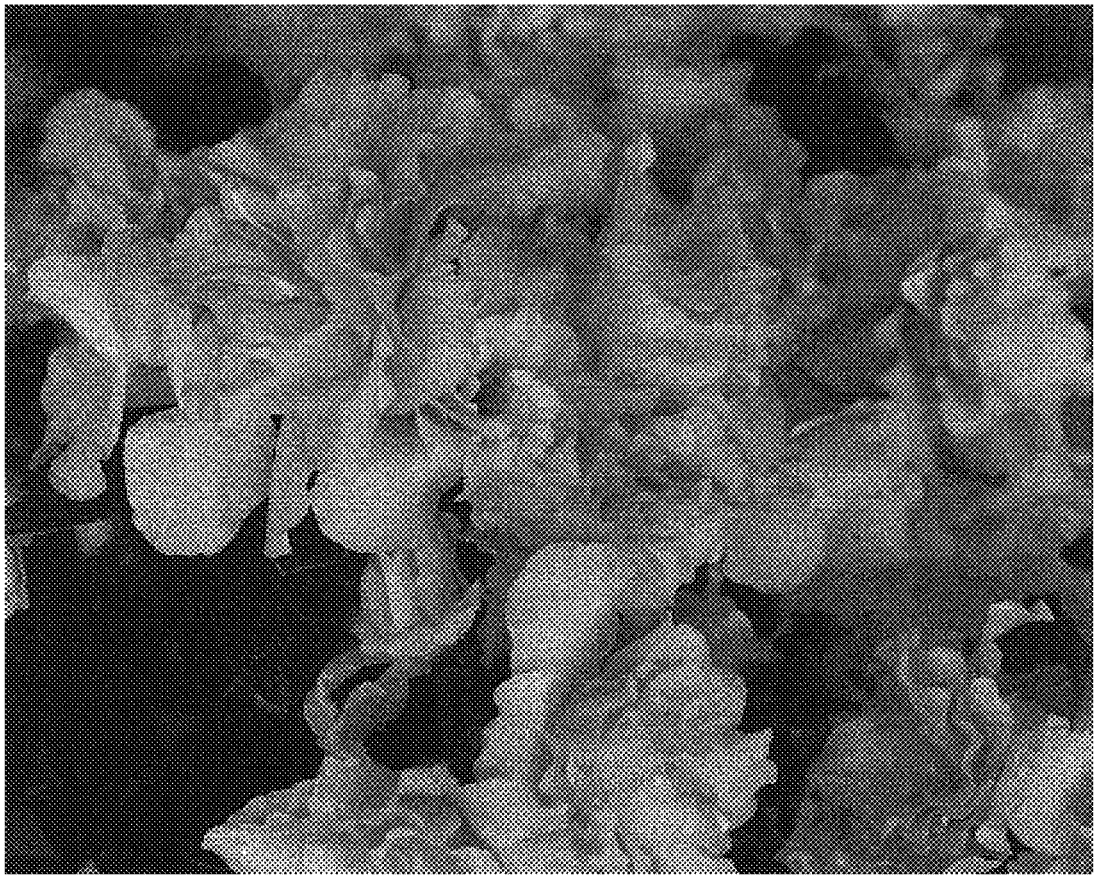

* * * * *